United States Patent [19]

Schwindeman

[11] Patent Number: 5,912,378
[45] Date of Patent: Jun. 15, 1999

[54] PROCESS FOR PREPARING TRIMETHYLSILYLOXY FUNCTIONALIZED ALKYLLITHIUM COMPOUNDS

[75] Inventor: James A. Schwindeman, Lincolnton, N.C.

[73] Assignee: FMC Corporation, Philadelphia, Pa.

[21] Appl. No.: 08/851,324

[22] Filed: May 5, 1997

Related U.S. Application Data

[63] Continuation of application No. 08/637,192, Apr. 8, 1996, abandoned, which is a continuation-in-part of application No. 08/341,822, Nov. 21, 1994, Pat. No. 5,543,540, which is a continuation-in-part of application No. 08/279,721, Jul. 25, 1994, Pat. No. 5,403,946.

[51] Int. Cl.$^6$ .................................. C07F 7/08; C07F 7/18
[52] U.S. Cl. ........................... 556/485; 556/482; 556/486
[58] Field of Search .................... 556/485, 486, 556/482

[56] References Cited

U.S. PATENT DOCUMENTS

| | | | |
|---|---|---|---|
| 2,381,138 | 8/1945 | Patnode et al. | 556/485 |
| 2,626,272 | 1/1953 | Speier | 556/485 |
| 3,511,865 | 5/1970 | Peterson . | |
| 5,082,961 | 1/1992 | Fukumoto et al. . | |
| 5,231,205 | 7/1993 | Rieke . | |
| 5,321,148 | 6/1994 | Schwindeman . | |
| 5,331,058 | 7/1994 | Shepherd et al. . | |
| 5,391,663 | 2/1995 | Bening et al. . | |
| 5,416,168 | 5/1995 | Willis et al. . | |

OTHER PUBLICATIONS

Chemical Abstracts, vol. 117, No. 3, 1992, Columbus, Ohio, US; abstract No. 26620m, XP002037339;& Magn. Reson. Chem., vol. 29, No. 12, 1991, pp. 1231–1232, H. Poleschner et al.
Chemical Abstracts, vol. 114, No. 21, 1991, Columbus, Ohio, US; abstract No. 207491d, XP002037340; & JP 02 270 887 A (Shin–Etsu Chemical Industry Co., Ltd.) Nov. 5, 1990.
Chemical Abstracts, vol. 98, No. 5, 1983, Columbus, Ohio, US; abstract No. 34230p, XP002037341; & RO 71 231 A (Institutul De Chimie, Cluj) Sep. 30, 1980.
Chemical Abstracts, vol. 94, No. 11, 1981, Columbus, Ohio, US; abstract No. 83571b, XP002037342; & Tetrahedron, vol. 36, No. 9, 1980, pp. 1215–1221, A. Commercon et al.
Chemical Abstracts, vol. 92, No. 1, 1980, Columbus, Ohio, US; abstract No. 6049u, XP002037343; & RO 64 552 A (Institutul de Chimie Cluj) Jul. 10, 1978.
Chemical Abstracts, vol. 86, No. 11, 1977, Columbus, Ohio, US; abstract No. 72743t, XP002037344; & Org. Prep. Proced. Int., vol. 8, No. 5, 1976, pp. 227–230, D.J. Voaden et al.
Chemical Abstracts, vol. 74, No. 5, 1971, Columbus, Ohio, US; abstract No. 22273w, XP002037345; & J. Org. Chem., vol. 35, No. 12, 1970, pp. 4241–4244, J.A. Mc–Closkey et al.
Journal of Organometallic Chemistry, vol. 150, 1978, pp. 187–201, XP002037336 P. Fostein et al: pp. 187–201.
J. Org. Chem., vol. 46, 1981, pp. 4389–4393, XP002037337 J.P. Marino et al: p. 4391, column 1.
Tetrahedron, vol. 41, No. 24, 1985, pp. 5887–5899, XP002037338 M. Gardette et al: p. 5889.

*Primary Examiner*—Paul F. Shaver
*Attorney, Agent, or Firm*—Alston & Bird LLP

[57] ABSTRACT

A process for producing compounds of the formula $(CH_3)_3SiORLi$, wherein R is selected from alkyl groups containing 2 to 10 carbon atoms and aryl groups containing 6 to 10 carbon atoms, by reacting, optionally in the presence of a catalyst, in an inert atmosphere, a haloalcohol of the formula HORX, wherein R is selected from alkyl groups containing 2 to 10 carbon atoms and aryl groups containing 6 to 10 carbon atoms and X is selected from chlorine or bromine, is reacted with neat hexamethyldisilazane at a temperature between 20° C. and 200° C., optionally in the presence of a catalyst, after which the resulting product, a trimethylsilyloxyalkylhalide compound, is reacted at a temperature between 50° C. and 160° C., with powdered lithium metal, in an inert hydrocarbon medium, to produce the $(CH_3)_3SiORLi$ compound.

9 Claims, No Drawings

PROCESS FOR PREPARING TRIMETHYLSILYLOXY FUNCTIONALIZED ALKYLLITHIUM COMPOUNDS

This application is a continuation of application Ser. No. 08/637,192, filed Apr. 8, 1996, now abandoned which is a continuation-in-part of Ser. No. 08/341,822 filed Nov. 21, 1994 U.S. Pat. No. 5,543,540 which is a continuation-in-part of Ser. No. 08/279,721 filed Jul. 25, 1994 U.S. Pat. No. 5,403,946.

The present invention concerns an improved process for preparing functionalized alkyllithium compounds of the formula $(CH_3)_3SiORLi$, novel trimethylsilyloxy alkyllithium compounds and novel intermediates used in the process.

Functionalized organolithium compounds have been used in organic synthesis reactions for some time and more recently have been used as initiators in the anionic polymerization of olefinic monomers. United Kingdom published patent application 2,241,239 discloses a process for producing initiators of the formula $R^1R^2R^3SiOALi$ wherein $R^1$, $R^2$ and $R^3$ are aliphatic and aromatic radicals and A is a hydrocarbon bridging group. This patent recommended using a 1.5 to 6 stoichiometric excess of lithium, an excess of 6 was used in the examples, to get high yields. Reaction temperatures below 50° C. were employed because above 40° C. undesired by-products were observed.

U.S. Pat. No. 5,321,148, issued Jun. 14, 1994 discloses a process for preparing functionalized alkyllithium compounds by reacting a fine particle size lithium metal of not more than 300 microns average particle size with an organosiloxyalkyl halide of the formula $R^1R^2R^3SiORX$ wherein $R^1$, $R^2$ and $R^3$ are independently selected from alkyl groups containing 1 to 10 carbon atoms and aryl groups containing 6 to 10 carbon atoms, R is selected from alkyl groups containing 1 to 8 carbon atoms either straight chain or substituted by alkyl or aryl groups, X is selected from chlorine or bromine, the reaction temperature is above 50° C, the reaction medium is a hydrocarbon solvent and the reaction is conducted in an inert atmosphere. The precursor, $R^1R^2R^3SiORX$, is prepared by reaction of an omega-halo alcohol HORX with $R^1R^2R^3SiCl$ and an acid acceptor, in a hydrocarbon solvent. Compounds of the formula $R^1R^2R^3SiORX$, when $R^1$, $R^2$ and $R^3$ are methyl, prepared according to the disclosed process, have been found to not uniformly lithiate, thus requiring more halide feed and resulting in slow filtration rates and lower than expected yields.

The present invention provides a process for producing compounds of the formula $(CH_3)_3SiORLi$ wherein R is selected from alkyl groups containing 2 to 10 carbon atoms and aryl groups containing 6 to 10 carbon atoms, by first reacting a haloalcohol of the formula HORX, wherein R has the meaning ascribed above and X is chlorine or bromine with hexamethyldisilazane, without solvent (neat). The resulting product, a trimethylsilyloxy-alkylhalide compound, is then reacted, in a second process step, with powdered lithium metal suspended in an inert liquid hydrocarbon solvent to produce the desired trimethylsilyloxyalkyllithium compound. The first step of the reaction can be done at temperatures from about 20° C. to 200° C.; the second step of the reaction is done at a temperature that is between 50° and 160° C. Both the first and second step of the process are conducted in an inert atmosphere. The first reaction can be catalyzed by a number of catalysts, for example hydrogen chloride, trimethylsilyl chloride, succinimide, saccharin, and barbituric acid.

Advantages of conducting the first step with no solvent include:
No solvent expense.
Faster reaction kinetics.
No need to strip solvent.
No waste solvent stream generated.
Product can be used directly in the subsequent reaction.
Extensive purification of the precursor eliminated.
Greater throughput per batch.

The haloalcohol is of the formula HORX, wherein R is selected from alkyl groups of 2 to 10 carbon atoms, straight chain or substituted by alkyl or aryl groups and aryl groups containing 6 to 10 carbon atoms and X is chloro or bromo. The trimethylsilyloxyalkylhalide compounds are produced by reaction of the haloalcohol with hexamethyldisilazane, with no solvent.

Trimethylsiloxyalkylhalides useful in the practice of this invention include but are not limited to 2-(trimethylsilyloxy)-1-ethyl halide, 3-(trimethylsilyloxy)-1-propyl halide, 3-(trimethylsilyloxy)-2-methyl-1-propyl halide, 3-(trimethylsilyloxy)-2,2-dimethyl-1-propyl halide, 4-(trimethylsilyloxy)-1-butyl halide, 5-(trimethylsilyloxy)-1- pentyl halide, 6-(trimethylsilyloxy)-1-hexyl halide, (4-(trimethylsilyloxymethyl)-cyclohexyl)-1-methyl halide, 8-(trimethylsilyloxy)-1-octyl halide, and the like.

The lithium metal is used in particulate or powder form of not greater than 300 micron average particle size and preferably 10 to 300 microns. The lithium typically contains 0.4 to 0.76 weight percent sodium and is used in at least stoichiometric amounts, preferably in excess of stoichiometric of 1 to 100% and preferably 20 to 40% excess. The lithium dispersion is prepared for use by washing several times with pentane or some other hydrocarbon solvent of choice, to remove the dispersing fluid, and preferably subjected to high speed agitation at elevated temperatures to condition the lithium for the reaction.

The second process step, the lithiation reaction, utilizes a temperature that is from at least 50° C. up to just below the decomposition temperature of the product, and preferably from 50° C. up to the boiling point of the solvent with reflux temperatures being most preferred. The optimal temperature for running the reaction can be exceeded by using only a high boiling solvent such as decane (BP-174° C.). The useful temperature range for operating the process is between about 50° C. and about 160° C. Reduced or elevated temperature can be employed if desired but are not required. The reactants and the products are not highly corrosive so many materials of construction can be used for the reactor and related process equipment.

The reaction solvent is an inert, liquid, non-polar hydrocarbon solvent selected from aliphatic, cycloaliphatic and aromatic hydrocarbons or mixtures thereof. Preferred solvents are aliphatic, cycloaliphatic and aromatic hydrocarbons, especially alkanes having 3 to 12 carbon atoms, cycloalkanes having 4 to 8 carbon atoms and aromatic hydrocarbons having 6 to 10 carbon atoms and mixtures thereof. The inert hydrocarbon medium includes but is not limited to pentane, hexane, cyclopentane, cyclohexane, methylcyclopentane, methylcyclohexane, heptane, methylcycloheptane, octane, decane, toluene, ethylbenzene, p-xylene, m-xylene, o-xylene, n-propylbenzene, 2-propylbenzene, n-butylbenzene, and t-butylbenzene, and mixtures thereof.

According to the process of the present invention, the precursor triorganosiloxyalkyl halide was prepared neat from the corresponding omega halo-alcohol, and hexamethyldisilazane. The lithium metal dispersion, when prepared in mineral oil, is washed free of mineral oil with a liquid hydrocarbon solvent, dried in a stream of argon and transferred to the reaction vessel with the hydrocarbon solvent. The mixture of clean metal and liquid hydrocarbon solvent was heated to the reaction temperature and the functionalized triorganosiloxyalkyl halide was added slowly to the heated lithium metal-hydrocarbon solvent mixture. An exotherm developed after 5–30% of the halide was added. The reaction temperature was controlled by external cooling of the reaction mixture. At the end of the halide feed, the reaction temperature rapidly declined to room temperature. The reaction mixture was stirred several hours at room temperature. At the end of the lithiation reaction, the reaction mixture was transferred to a sintered glass filter through which the solution was filtered rapidly with 3 psi ($20.68 \times 10^3$ Pa) argon pressure. After the insolubles were removed by filtration, the filtrate was an essentially pure solution of the trimethylsiloxyalkyllithium compound. The resultant non-turbid solution was analyzed for total base, active carbon-lithium (modified Watson-Estham titration) and inorganic halide.

Trimethylsilyloxyalkyl lithium compounds which can be prepared by the process of this invention include but are not limited to 3-(trimethylsilyloxy)-1-propyl lithium, 3-(trimethylsilyloxy)-2-methyl-1-propyl lithium, 4-(trimethylsilyloxy)-1-butyl lithium, 5-(trimethylsilyloxy)-1-pentyl lithium, 6-(trimethylsilyloxy)-1-hexyl lithium, (4-(trimethylsilyloxymethyl)-cyclohexyl)-1-methyl lithium, 8-(trimethylsilyloxy)-1-octyl lithium and the like.

The following examples further illustrate the invention.

PREPARATION OF HALOORGANOSILYLOXYALKANE MATERIALS

1. Preparation of 3-Chloro-2,2-dimethyl-1-trimethylsilyloxy-propane at 150° C., Lot 9277

A 500 milliliter, three-necked flask was fitted with a large magnetic stir bar, a reflux condenser, a thermocouple attached to a THERM-O-WATCH®, a 125 ml. pressure-equalizing addition funnel, and an argon inlet. This apparatus was dried in an oven overnight at 125° C., assembled hot, and allowed to cool to room temperature in a stream of argon. The flask was charged with 122.58 grams (1.00 mole, 1.00 equivalent) of 3-chloro-2,2-dimethyl-1-propanol. Hexamethyldisilazane, 83.24 grams (0.516 mole, 0.516 equivalent), was then added rapidly dropwise via the addition funnel. Trimethylsilylchloride catalyst, one ml., was added via a syringe. An immediate exotherm of 21.7° C. was observed. A white precipitate also formed when the catalyst was added. The reaction mixture was heated to 150° C. with a heating mantle, controlled by the THERM-O-WATCH®. After ninety minutes at this temperature, all the solids had dissolved. The heat source was removed. The reaction mixture was analyzed by Gas Chromatography (GC), thirty meter X 0.53 mm AT-1 column. All the starting 3-chloro-2,2-dimethyl-1-propanol had been consumed, with the formation of a single, higher-boiling component. After the reaction mixture had cooled to room temperature, it was transferred to a medium porosity sintered glass filter. The filtrate was collected in a dry 250 ml. bottle. This afforded a clear, very pale yellow solution, yield=188.84 grams (97.0% yield). GC assay=97.5% desired product, and 2.5% unknowns.

2. Preparation of 3-Chloro-2,2-dimethyl-1-trimethylsilyloxy-propane at 100° C, Lot 9279

A 500 milliliter, three-necked flask was fitted with a large magnetic stir bar, a reflux condenser, a thermocouple attached to a THERM-O-WATCH®, a 125 ml. pressure-equalizing addition funnel, and an argon inlet. This apparatus was dried in an oven overnight at 125° C., assembled hot, and allowed to cool to room temperature in a stream of argon. The flask was charged with 122.68 grams (1.00 mole, 1.00 equivalent) of 3-chloro-2,2-dimethyl-1-propanol. Hexamethyldisilazane, 83.35 grams (0.516 mole, 0.516 equivalent), was then added dropwise via the addition funnel. Trimethylsilylchloride catalyst, one ml., was added via a syringe. An immediate exotherm of 23.4° C. was observed. A white precipitate also formed when the catalyst was added. The reaction mixture was heated to 100° C with a heating mantle, controlled by the THERM-O-WATCH®. Periodically, an aliquot was removed, filtered through a 0.45 micron syringe filter, and analyzed by Gas Chromatography (GC), thirty meter X 0.53 mm AT-1 column. After twenty-four hours at 100° C., both of the starting materials were still present. Therefore, an additional 0.5 ml. of trimethylsilylchloride was added. After forty-eight hours at 100° C, both of the starting materials were still present. Therefore, an additional 0.5 ml. of trimethylsilylchloride was added. After a total of seventy-two hours at 100° C, all the starting 3-chloro-2,2-dimethyl-1-propanol had been consumed, with the formation of a single, higher-boiling component. The heat source was removed. After the reaction mixture had cooled to room temperature, it was transferred to a medium porosity sintered glass filter. The filtrate was collected in a dry 250 ml. bottle. This afforded a clear, very pale yellow solution, yield=178.37 grams (91.65% yield). GC assay= 96.8% desired product, 0.1% hexamethyldisilazane, and 3.1% unknowns.

B. PREPARATION OF TRIMETHYLSILYLOXYALKYLLITHIUM COMPOUNDS

1. Preparation of 2,2-Dimethyl-3-trimethylsilyloxy-1-propyllithium Lot 9291

A 500 ml., three-necked flask was equipped with a mechanical stirrer, a 125 ml. pressure-equalizing addition funnel, and a Claisen adapter fitted with a dry ice condenser, a thermocouple, and an argon inlet. This apparatus was dried in an oven overnight at 125° C., assembled hot, and allowed to cool to room temperature in a stream of argon. Lithium dispersion was washed free of mineral oil with hexane (2×70 ml.), and pentane (1×70 ml.), then dried in a stream of argon. The dry lithium powder, 6.80 grams (0.980 mole, 2.80 equivalents) was transferred to the reaction flask with 280 ml. cyclohexane. This slurry was stirred at 450 RPMs, and heated to 64.7° C. with a heating mantle. The heat source was removed. 3-Chloro-2,2-dimethyl-1 -trimethylsilyloxy-propane, 68.10 grams (Lot 9277, 0.350 mole, 1.00 equivalent) was then added dropwise to the reaction mixture. An exotherm was noted after 12.3% of the feed had been added. A dry ice/hexane cooling bath was employed to maintain the reaction temperature at 60–65° C. The total halide feed time was eighty-five minutes. The reaction temperature rapidly fell off at the end of the halide feed. The reaction mixture was stirred at room temperature for seventy minutes, then transferred to a small, sintered glass filter. The product filtered rapidly with 2 psi argon. The muds were reslurried with cyclohexane (2×60 ml.). This afforded a pale yellow solution, yield=450 ml., 352.05 grams.

Total base=15.6 wt. %.

Active C-Li=15.3 wt. %.

Soluble chloride=182 ppm.

Yield based on active C-Li=92.6%.

2. Preparation of 2,2-Dimethyl-3-trimethylsilyloxy-1-propyllithium Lot 9295

A 500 ml., three-necked flask was equipped with a mechanical stirrer, a 125 ml. pressure-equalizing addition funnel, and a Claisen adapter fitted with a dry ice condenser, a thermocouple, and an argon inlet. This apparatus was dried in an oven overnight at 125° C., assembled hot, and allowed to cool to room temperature in a stream of argon. Lithium dispersion was washed free of mineral oil with hexane (2×70 ml.), and pentane (1×70 ml.), then dried in a stream of argon. The dry lithium powder, 6.50 grams (0.936 mole, 2.80 equivalents) was transferred to the reaction flask with 280 ml. cyclohexane. This slurry was stirred at 450 RPMs, and heated to 64.7° C. with a heating mantle. The heat source was removed. 3-Chloro-2,2-dimethyl-1-trimethylsilyloxy-propane, 65.09 grams (Lot 9277, 0.334 mole, 1.00 equivalent) was then added dropwise to the reaction mixture. An exotherm was noted after 9.6% of the feed had been added. A dry ice/hexane cooling bath was employed to maintain the reaction temperature at 60–65° C. The total halide feed time was ninety-one minutes. The reaction temperature rapidly fell off at the end of the halide feed. The reaction mixture was stirred at room temperature for ninety minutes, then transferred to a small, sintered glass filter. The product filtered rapidly with 2 psi argon. The muds were reslurried with cyclohexane (2×50 ml.). This afforded a pale yellow solution, yield=430 ml., 335.10 grams.

Total base=15.5 wt. %.

Active C-Li=15.3 wt. %.

Yield based on active C-Li=92.4%.

C. COMPARATIVE EXAMPLE

1. Preparation of 3-Chloro-2,2-dimethyl-1-trimethylsilyloxy-propane in Cyclohexane Solution, Lot 9103

A one liter, three-necked flask was fitted with a large magnetic stir bar, a reflux condenser, a teflon clad thermocouple, a 125 ml. pressure-equalizing addition funnel, and an argon inlet. This apparatus was dried in an oven overnight at 125° C., assembled hot, and allowed to cool to room temperature in a stream of argon. The flask was charged with 122.60 grams (1.00 mole, 1.00 equivalent) of 3-chloro-2,2-dimethyl-1-propanol, and 250 ml. of cyclohexane. This afforded a homogenous solution. Hexamethyldisilazane, 85.54 grams (0.53 mole, 0.53 equivalent) was then added dropwise. There was an initial endotherm, then the temperature slowly elevated. Total feed time was seventy minutes. The catalyst, trimethylsilylchloride (0.5 ml.) was then added with a pipette. A white precipitate formed immediately. The reaction flask was swept with a slight positive flow of argon, above the level of the liquid. The reaction mixture was heated to reflux with a heating mantle. Ammonia fumes were detected exiting from the apparatus with pH paper before reflux was achieved. After three hours at reflux, the reaction mixture was clear and homogenous. After five and a half hours heating, the heat source was removed. After six hours, an aliquot was removed, and analyzed by Gas Chromatography (GC), thirty meter X 0.53 mm AT-1 column. The conversion to the desired product was 64.2%. The reaction mixture was again heated to reflux, and held at reflux overnight. In the morning, the heat source was again removed, and the reaction was reanalyzed by GC. Very little change in composition was detected by GC. 3-Chloro-2,2-dimethyl-1-propanol and hexamethyldisilazane were both still present in the reaction mixture. Therefore, an additional 0.5 ml. of trimethylsilyl-chloride was added to the reaction flask. A white precipitate was again observed. The reaction mixture was heated to reflux for an additional six hours, then allowed to cool to room temperature. All the starting material had been consumed. The reaction mixture was transferred to a dry, 500 ml. single-necked flask. The product was purified by distillation through a six inch Vigreux column.

The desired product had a boiling point of 169.8–175.0° C.

This afforded a clear, colorless oil, yield=183.07 grams, 94.1%.

GC analysis of this material indicated it was 98.9% desired product, 0.6% hexamethyldisilazane, and 0.5% unknowns.

The comparison example shows the superiority of performing the trimethylsilation reaction without solvent. The neat reaction featured faster reaction rates, easier work-up, and no need for extensive product purification by distillation.

I claim:

1. A trimethylsilyloxyalkyl halide of the formula $(CH_3)_3SiORX$ wherein R is selected from branched or cyclic alkyl groups containing 3 to 10 carbon atoms and aryl groups containing 6 to 10 carbon atoms and X is selected from bromide and chloride, wherein said branched or cyclic alkyl groups further comprise at least 3 carbon atoms bridging O and X.

2. A trimethylsiloxyalkyl halide of claim 1 wherein the trimethylsiloxyalkyl halide is selected from the group consisting of 3-(trimethylsiloxy)-2-methyl-1-propyl halide, (4-(trimethylsiloxy)-cyclohexyl)-1-methyl halide, and 3-(trimethylsiloxy)-2,2-dimethyl-1-propyl halide.

3. A trimethylsilyloxyalkyl halide of claim 2 wherein the halide is selected from the group consisting of chloride and bromide.

4. A trimethylsilyloxyalkyl lithium compound of the formula $(CH_3)_3SiORLi$ wherein R is selected from alkyl groups containing 3 to 10 carbon atoms and aryl groups containing 6 to 10 carbon atoms.

5. A trimethylsilyloxyalkyl lithium compound of claim 4 wherein the trimethylsilyloxyalkyl lithium compound is selected from the group consisting of 3-(trimethylsilyloxy)-1-propyl lithium, 3-(trimethylsilyloxy)-2-methyl-1-propyl lithium, 4-(trimethylsilyloxy)-1-butyl lithium, 5-(trimethylsilyloxy)-1-pentyl lithium, 6-(trimethylsilyloxy)-1-hexyl lithium, (4-(trimethylsilyloxymethyl)-cyclohexyl)-1-methyl lithium and 8-(trimethylsilyloxy)-1-octyl lithium.

6. A trimethylsilyloxyalkyl halide product of the formula $(CH_3)_3SiORX$, wherein R is selected from the group consisting of branched or cyclic alkyl groups containing 3 to 10 carbon atoms and aryl groups containing 6 to 10 carbon atoms, and X is selected from bromide and chloride, wherein said branched or cyclic alkyl groups contain at least 3 carbon atoms bridging O and X, produced by a process comprising reacting, in an inert atmosphere, a haloalcohol of the formula HORX, wherein R and X are as defined above with neat hexamethyldisilazane at a temperature between 20° C. and 200° C., optionally in the presence of a catalyst.

7. The product of the process of claim 6 further comprising employing an effective amount of a catalyst in the reaction.

8. The product of the process of claim 7 wherein the catalyst is selected from the group consisting of hydrogen chloride, trimethylsilyl chloride, succinimide, saccharin, and barbituric acid.

9. The product of the process of claim 6 wherein the omega- halo alcohol is reacted neat with hexamethyldisilazane at a temperature between 100° C and 180° C.

* * * * *